United States Patent [19]
Nicolaou et al.

[11] Patent Number: 5,643,887
[45] Date of Patent: Jul. 1, 1997

[54] DAUNOMYCIN DERIVATIVE WITH REDUCED CYTOTOXICITY TOWARD NORMAL CELLS

[75] Inventors: Kyriacos C. Nicolaou; Wolfgang A. Wrasidlo; Peter E. Maligres, all of La Jolla, Calif.

[73] Assignee: The Scripps Research Institute, LaJolla, Calif.

[21] Appl. No.: 423,266

[22] Filed: Apr. 17, 1995

Related U.S. Application Data

[63] Continuation of Ser. No. 922,834, Jul. 31, 1992, Pat. No. 5,413,992.
[51] Int. Cl.$^6$ ............................................. A61K 31/70
[52] U.S. Cl. ............................................. 514/34
[58] Field of Search ............................................. 514/34

[56] References Cited

U.S. PATENT DOCUMENTS

| | | | |
|---|---|---|---|
| 4,973,674 | 11/1990 | Brasca et al. | 536/6.4 |
| 4,973,675 | 11/1990 | Israel et al. | 536/6.4 |
| 5,413,992 | 5/1995 | Nicolaou et al. | 514/34 |

OTHER PUBLICATIONS

Johnson et al., *The clinical impact of screening and other experimental tumor studies*, Cancer Treatment Reviews, 2:1–31 (1975).

*Primary Examiner*—Elli Peselev
*Attorney, Agent, or Firm*—Welsh & Katz Ltd.

[57] ABSTRACT

Chemotherapeutic agents that exhibit cytotoxicity similar to that of daunomycin against cancer cells, but exhibit lessened cytotoxicity against normal, non-transformed cells are disclosed, as are compositions, processes for making and using the same. A contemplated chemotherapeutic agent is a daunomycin derivative whose structure corresponds to structural Formula I, wherein Ar is phenyl, 1-naphthyl or 2-naphthyl

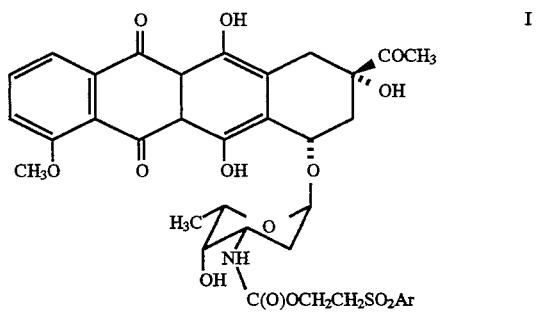

4 Claims, 1 Drawing Sheet

DAUNOMYCIN DERIVATIVE WITH REDUCED CYTOTOXICITY TOWARD NORMAL CELLS

GOVERNMENTAL SUPPORT AND RIGHTS

This invention was made with government support under Contract No. CA 46446 awarded by the National Institutes of Health. The government has certain rights in the invention.

CROSS-REFERENCE TO RELATED APPLICATION

This is a division of application Ser. No. 07/922,834, filed Jul. 31, 1992, now U.S. Pat. No. 5,413,992.

TECHNICAL FIELD

The present invention relates to a derivative of daunomycin, and more particularly to a daunomycin derivative that exhibits reduced cytotoxicity against normal, non-transformed cells while maintaining a cytotoxicity against cancerous cells that is similar to daunomycin itself.

BACKGROUND ART

Daunomycin, also known as daunorubicin leukaemomycin C, rubidomycin and Cerubidin, is an antibiotic of the rhodomycin group that is isolated from fermentation of *Streptomyces peucetias*. The total synthesis of the molecule has also been reported. Acton et al., *J. Med. Chem.*, 17:659 (1974).

The daunomycin molecule is composed of two parts. The first part, a tetracyclic aglycone, is referred to as daunomycinone, and is glycosidically linked to the second part, an amino sugar, that is referred to as daunosamine (3-amino-2,3,6-trideoxy-L-lyxohexose).

Daunomycin is usually used clinically in acute leukemias and less frequently for other cancers. For example, daunomycin is particularly effective in inducing remission in children with acute lymphoblastic leukemia, and is a widely used drug for treating adults with nonlymphocytic leukemias. Daunomycin is also used in treating children having solid tumors and for treating lymphomas. Daunomycin has been found to intercalate into DNA, with resulting impairment of DNA and RNA syntheses. Double- and single-strand breaks in DNA have been noted as a result of treatment with daunomycin.

As with many chemotherapeutic agents, daunomycin kills normal cells as well as cancerous cells. It would therefore be beneficial if a daunomycin derivative could be found that exhibited a cytotoxicity against cancerous cells that was similar to daunomycin itself, but that exhibited a reduced cytotoxicity against normal, non-cancerous (non-transformed) cells.

BRIEF SUMMARY OF THE INVENTION

The present invention contemplates a daunomycin derivative that exhibits reduced cytotoxicity against normal cells relative to daunomycin, but exhibits a cytotoxic potency against cancerous cells similar to that of daunomycin. A contemplated daunomycin derivative corresponds in structure to structural Formula I, below,

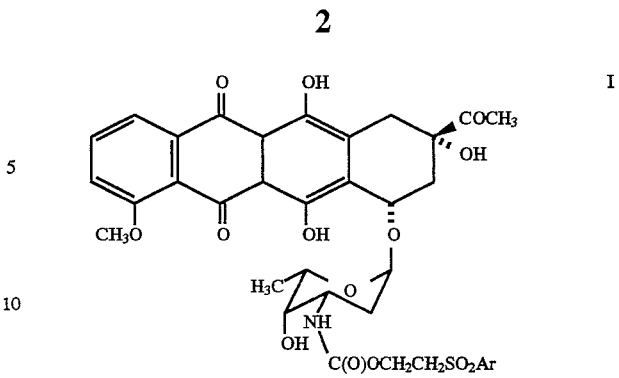

wherein Ar is phenyl, 1-naphthyl or 2-naphthyl, phenyl being particularly preferred.

Also contemplated is a pharmaceutical composition containing a chemotherapeutic amount of a before-described compound dissolved or dispersed in a physiologically tolerable diluent.

A chemotherapeutic process for treating a cancerous condition such as leukemia or a carcinoma is also contemplated. In accordance with this process, cancerous cells that are to be killed or whose growth is to be inhibited are contacted in an aqueous medium suitable for growth of those cells with a chemotherapeutic amount of a before-described daunomycin derivative, preferably in a pharmaceutical composition as active agent dissolved or dispersed in a physiologically tolerable diluent. That contact is maintained in an aqueous medium for a time sufficient for the cancer cells to be killed or their growth retarded. Multiple contacting; i.e., the use of a plurality of administrations, of the pharmaceutical composition is particularly contemplated for in vivo uses.

The present invention has several benefits and advantages.

One salient benefit of the invention is that the cytotoxicity of a before-discussed daunomycin derivative against normal cells such as human peripheral blood lymphocytes (PBL), human dermal fibroblasts (HDF), and human mammary epithelial cells (HMEC) is about 30 to about 70 times less than that exhibited by daunomycin itself.

An advantage of the invention is that cytotoxicity against transformed, cancerous cells such as leukemia, and carcinoma cell lines such as the Molt-4, HT-29, Capan-1, Ovcar-3 and UCLAP3 cell lines for a before-discussed daunomycin derivative is similar to that of daunomycin.

Another benefit of the present invention is that its compounds are readily prepared from daunomycin, a commercially available chemotherapeutic agent.

Still further benefits and advantages of the present invention will become apparent to those skilled in the art from the discussion that follows.

DETAILED DESCRIPTION OF THE INVENTION

I. Compounds

Figure 1:
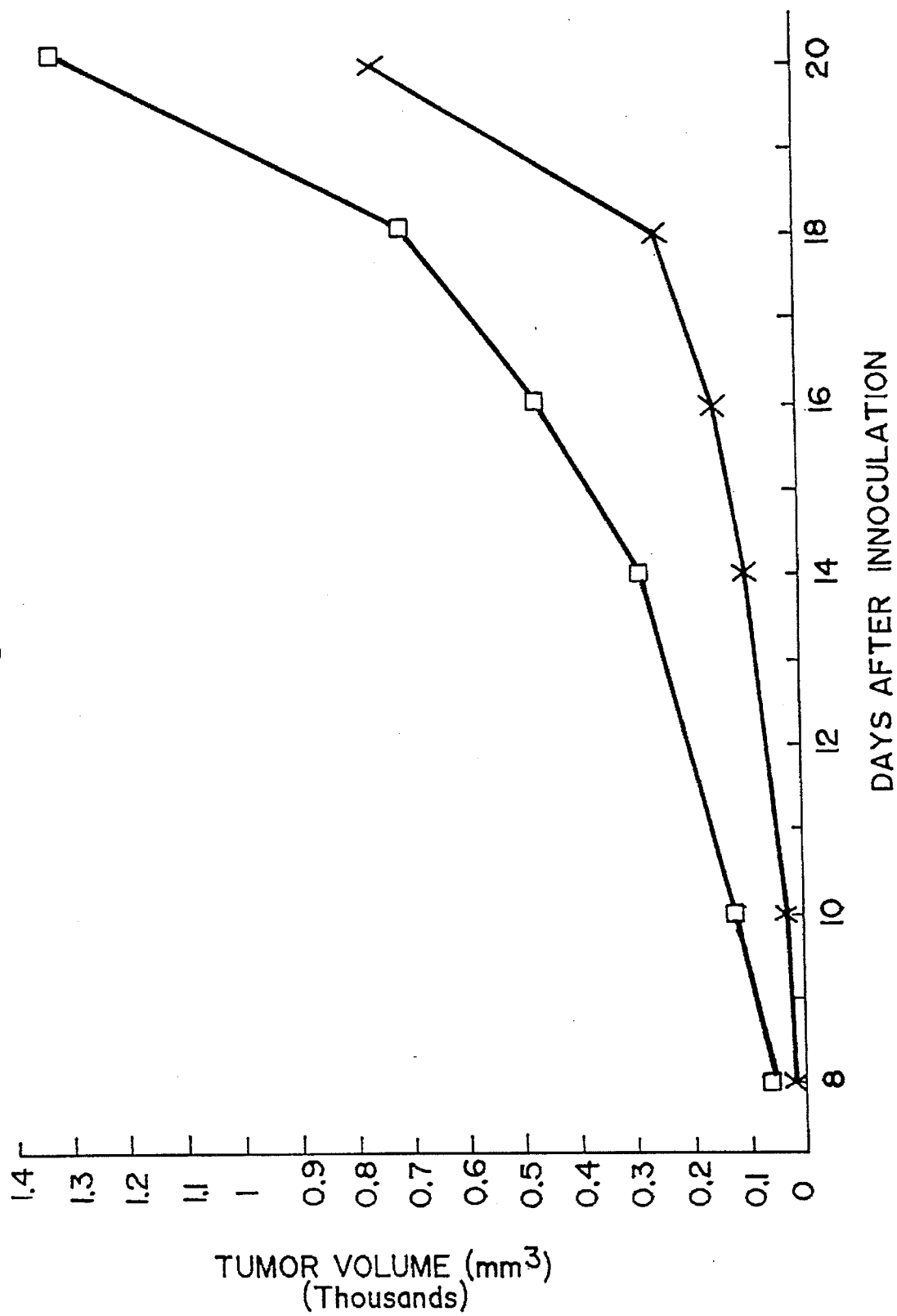
FIG. 1 is a graph showing the average tumor size in 6–10 week old female Balb/c BYJ mice inoculated with EMT-6 mammary tumor cells. Control mice (open squares) were treated with normal saline on days 1, 5 and 9 after inoculation. Study mice (X's) were treated with an equal volume of normal saline containing 15 mg/kg of Compound I on those same days post inoculation with the tumor cells.

The present invention contemplates a novel arylsulfonylethyleneoxycarbonyl or 2-(arylsulfonyl)ethylcarbamate derivative of daunomycin having a structure that corresponds to that of Formula I, below, where Ar is phenyl, 1-naphthyl or 2-naphthyl.

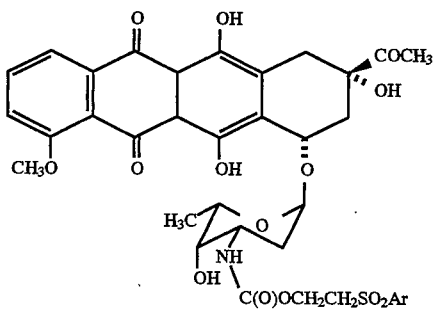

In preferred practice, Ar is phenyl (Ph) so that a preferred contemplated compound has a structure that is shown below for Compound 1. Compound 1 is more formally named hereinafter.

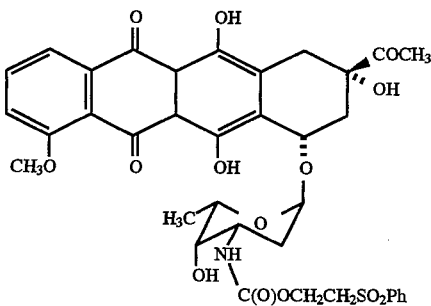

Compound 1

A compound of the invention is useful in treating cancerous conditions as is daunomycin. However, a contemplated compound exhibits less cytotoxicity toward non-cancerous cells than does daunomycin, while exhibiting similar potency; i.e., about equal to about one-fourth, to daunomycin against several leukemia, carcinoma and other transformed, cancerous cell lines, based on $IC_{50}$ values. Exemplary $IC_{50}$ data for Compound 12 and daunomycin are shown in Table 1, below.

TABLE 1*

| Cell Lines | $IC_{50}$ Values (M×10⁷) | |
|---|---|---|
| | Compound 1 | Daunomycin |
| Transformed | | |
| HL-60 (promyelocytic leukemia) | 0.98 | <0.98 |
| HT-29 (colon carcinoma) | 7.8 | 7.8 |
| MCF-7 (breast carcinoma) | 7.8 | 7.8 |
| MOLT-4 (T cell leukemia) | 0.01 | 0.01 |
| SK-Mel-28 (melanoma) | 31 | 16 |
| Copan-1 (pancreatic carcinoma) | 7.8 | 3.9 |
| P-388 (mouse leukemia) | 7.8 | 3.9 |
| Ovcar-3 (ovarian carcinoma) | 16 | 3.9 |
| UCLA-P3 (lung carcinoma) | 31 | 7.3 |
| Non-Transformed | | |
| HMEC | 130 | 3.9 |
| NHDF | 130 | 1.9 |
| CHO | 63 | 3.9 |
| PBL | 250 | 7.8 |

*Methods by which the above data were obtained and cell sources are discussed in detail hereinafter.

As can be seen from the above in vitro data, Compound 1 and daunomycin exhibited the same potencies against the first four cancer cell lines (two leukemias and two carcinomas). Compound 1 had about one-half the potency of daunomycin against the second three cancer cell lines (melanoma, pancreatic carcinoma and mouse leukemia), and about one-fourth the potency of daunomycin against the final two carcinoma cells lines.

Surprisingly, Compound 1 was much less toxic than daunomycin when assayed against four normal, non-transformed types of cells. Thus, whereas there was no difference to a four-fold difference between the compounds for cancer cell cytotoxicity difference, daunomycin was about 15- to 70-fold more toxic to the normal cells than was Compound 1.

Daunomycin has a reported $LD_{50}$ in mice of 20 mg/kg when administered intravenously (i.v.) and 5 mg/kg when administered intraperitoneally (i.p.) [Merck Index, 11th ed., Merck & Co., Inc., Rahway, N.J., page 445 (1989)]. Using i.p. injections, the $LD_{50}$ value in mice for daunomycin was here found to be about 12 mg/kg, Whereas that for Compound 1 was found to be about 35 mg/kg.

Thus, the lessened in vitro cytotoxicity observed for a compound of the invention as compared to daunomycin was qualitatively borne out in vivo by the $LD_{50}$ studies. A further in vivo study, whose results are illustrated in FIG. 1 and discussed in detail hereinafter, showed that Compound 1 retarded the growth of mammary tumors (cell line EMT-6) implanted in mice.

The reason that a compound of the invention exhibits its differing cytotoxicities between normal and cancerous cells and the mode of action of such a compound are unknown. Without wishing to be bound by theory, it is believed that the presence of the urethane-linked group generally deactivates the compound toward cytotoxicity, as is the case for N-acylation of daunomycin. Once absorbed into a cell, a cellular protein is thought to abstract a proton adjacent to the sulfonyl group which causes a β-elimination and fragmentation to occur that ultimately provides free daunomycin within the cell. That free daunomycin, once within the cell exhibits cytotoxicity as daunomycin normally does in a cell.

It is further believed that cancerous cells such as leukemia and carcinoma cells have a greater quantity or a more active form of that cellular deprotonating protein than do normal cells, thereby providing for the observed differences in cytotoxicity. A candidate deprotonating protein is being sought.

Phenyl- and 1- and 2-naphthylsulfonylethyleneoxycarbonyl groups have been utilized by Nicolaou and co-workers as triggering agents for enediyne analogs of dynemicin A. See, for instance Nicolaou et al., Science, 256:1172 (1992), and the citations therein. In those uses, the free endocyclic secondary amine-containing dynemicin analog formed by removal of the urethane group becomes relatively unstable, and that compound becomes susceptible to cyclorearrangement. Here, of course, daunomycin is itself stable. Thus, the same group functions differently on the respective dynemicin A analog and present molecules.

The mechanism by which the dynemicin A analogs act to cleave DNA is thought to involve bonds being made and broken to the resulting endocyclic secondary amine group that is freed when the urethane link is broken. That amine group bonding and rebonding contributes to the opening of an epoxide and subsequent reaction of the molecule with DNA. The daunomycin amine group cannot play a similar mechanistic role because of its presence exocyclic to a saturated ring, and because there is no adjacent epoxide present whose opening can be affected to lead to a cyclorearranged product. Thus, the mechanism of action of the dynemicin A analogs is different from that of the present daunomycin derivatives, although both types of compound can contain the same phenyl- or naphthylsulfonylethyleneoxycarbonyl group.

The two above differences, (i) function of the group stabilization of the active agent versus deactivation of the active agent, and (ii) mechanisms of active agent reaction, notwithstanding, the phenyl- and both naphthylsulfonylethyleneoxycarbonyl groups of the dynemicin A analogs behave similarly in in vitro, and appear to fragment similarly to a daunomycin derivative herein.

II. Pharmaceutical Compositions

A compound of the invention is useful as a chemotherapeutic agent in treating cancerous conditions such as leukemias and carcinomas as is daunomycin. A compound of the invention can also therefore be referred to as an "active agent" or "active ingredient".

A pharmaceutical composition is thus contemplated that contains a before-described compound of the invention as active agent. A pharmaceutical composition is prepared by any of the methods well known in the art of pharmacy all of which involve bringing into association the active compound and the carrier therefor. For therapeutic use, a compound of the present invention can be administered in the form of conventional pharmaceutical compositions. Such compositions can be formulated so as to be suitable for oral or parenteral administration, or as suppositories, parenteral administration being preferred. In these compositions, the agent is typically dissolved or dispersed in a physiologically tolerable carrier.

A carrier or diluent is a material useful for administering the active compound and must be "pharmaceutically acceptable" in the sense of being compatible with the other ingredients of the composition and not deleterious to the recipient thereof. As used herein, the phrases "physiologically tolerable" and "pharmaceutically acceptable" are used interchangeably and refer to molecular entities and compositions that do not produce an allergic or similar untoward reaction, such as gastric upset, dizziness and the like, when administered to a host mammal, such as a mouse, rat or other laboratory mammal, or to a human host. The physiologically tolerable carrier can take a wide variety of forms depending upon the preparation desired for administration and the intended route of administration.

As an example of a useful composition, a compound of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Mack Publishing Co., Easton, Pa. (1980).

An active agent can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Ed., *Methods in cell Biology*, Vol. XIV, Academic press, New York, N.Y. (1976), p.33 et seq.

An active agent can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as buffers, flavoring agents, binders, surface active agents, thickeners, lubricants, preservatives (including antioxidants) and the like, and substances included for the purpose of rendering the formulation isotonic with the blood of the intended recipient host mammal.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the active agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A compound of the invention is present in such a pharmaceutical composition in an amount effective to achieve the desired result in treating a cancerous condition. That amount is referred to as a chemotherapeutic amount.

Exemplary in vivo dose regimens useful herein are similar to those utilized for daunomycin, with the chemotherapeutic amount (dosage) being about the same to about three-times that used for daunomycin. Exemplary dosages include about 15 to 180 milligrams per square meter of host (mg/sq m) daily for three days or weekly, and also about 0.8 to 3.0 mg/kg daily for 3–6 days. Dosages nearer the $LD_{50}$ value can also be used such as about 15 mg/kg at four to five day intervals. As is well known in the art, specific dosages, particularly in humans, are left to the treating physician and depend upon the cancerous condition treated, patient tolerance, and the like.

III. Processes

A compound of the invention is useful in as a cytotoxic agent and also in inhibiting the growth of neoplastic cells, and is utilized in a process for effecting such a result. A compound of the invention is typically utilized in a before-described pharmaceutical composition.

In accordance with such a process, target cancerous (neoplastic) cells to be killed or whose growth is to be inhibited are contacted in an aqueous medium suitable for growth of those cells with a chemotherapeutic amount effective or sufficient for such a purpose of a before-discussed daunomycin derivative that is preferably present in a before-discussed pharmaceutical composition as active ingredient dissolved or dispersed in a physiologically tolerable (pharmaceutically acceptable) diluent. That contact is maintained in the aqueous medium for a time sufficient for the desired result to be obtained; i.e., cancer cells killed or neoplastic cell growth inhibited.

Where the desired result is carried out in vitro, contact is carried out by simply admixing the target cells with the composition in the aqueous medium and maintaining them together under the appropriate culture conditions for usual cell growth to occur, as for control, untreated cells. Culture conditions such as pH value, osmolality, temperature and the presence of appropriate nutrients for an aqueous medium suitable for growth of those cells are well known to skilled workers. Thus, a single admixing and contacting is typically sufficient for in vitro purposes.

The above process is also useful in vivo, as where a mammal such as a rodent like a rat, mouse, or rabbit, a farm animal like a horse, cow or goat, or a primate like a monkey, ape or human is treated. Here, the aqueous medium contacting of a contemplated daunomycin derivative and the cancer cells to be killed or whose growth is to be inhibited is typically achieved by administration of a pharmaceutical composition to the mammal by oral, nasal or anal administration or by introduction intravenously, subcutaneously or intraperitoneally. Thus, contact in vivo is achieved via the blood, lymph system or other body fluid, which also provide the aqueous medium for that contacting that is also suitable for growth of the cells.

Although a single administration (admixture) and its resulting contact is usually sufficient to maintain the required contact and obtain a desired result in vitro, multiple administrations; i.e., where the target cancer cells are contacted a plurality of times, are typically utilized in vivo. Thus, because of a body's breakdown and excreting pathways, contact between an active ingredient of a preferred pharmaceutical composition and the target cancer cells is typically maintained by repeated administration of a pharmaceutical composition over a period of time such as days, weeks or months, or more, depending upon the target cells.

Exemplary concentrations for in vitro cytotoxicity studies vary with the cells to be killed, and can range from about $10^{-5}$M to about $10^{-10}$M, as is seen from the $IC_{50}$ data in Table 1 hereinbefore. Exemplary concentrations and dosages for in vivo usage are discussed hereinbefore.

A compound of the invention can also be used in conjunction with other drugs commonly utilized with daunomycin. Those other drugs are used in their usual amounts and dosage regimens. For example, daunomycin is frequently used in combination with vincristine and prednisone for treatment of acute lymphoblastic leukemia in children, and those latter two drugs can be used in combination with a compound of the invention in a present process.

Assays for cell death are readily carried out in vitro as discussed hereinafter by using $IC_{50}$ studies. Assays for in vivo cancel cell killing are more complex, but are well known to oncologists.

Complete remission from the disease as by an absence of leukemic cells in the marrow and peripheral blood, or absence of a tumor such as a carcinoma is the desired result. Partial remissions as in a change from an $M_4$ stage in acute leukemia to an $M_2$ stage for marrow infiltration by blast cells and a return to normal hemopoiesis are also useful. A reduction in tumor size or a slowing of the normal rate of tumor growth by about one-half or more are also useful assays.

IV. Syntheses

A compound of the invention can be readily prepared. In one exemplary synthesis 2-(phenylsulfonyl)ethoxycarbonyl chloride was reacted with daunomycin hydrochloride in dichloromethane and pyridine to form Compound 1 as is discussed in detail hereinafter. 2(1- or 2-Naphthylsulfonyl) ethoxycarbonyl chloride can be similarly reacted to form the corresponding naphthyl group-containing derivatives of daunomycin.

Best Mode for Carrying Out the Invention

Compound Synthesis

8-Acetyl-10-[[3-[N-[2-(phenylsulfonyl)-ethoxycarbonyl]amino-2,4,6-trideoxy-1-lyxo-hexapyranosyl]oxy]-7,8,9,10-tetrahydro-6,8,11-trihydroxy-1-methoxy-5,12-naphthacenedione; N-[2-(phenylsulfonyl) ethoxycarbonyl]-daunomycin (Compound 1)

To a solution of 2-phenylsulfonylethanol (223 mg, 1.20 mmol) and bistrichloromethylcarbonate (triphosgene) (119 mg, 0.40 mmol) in dichloromethane (5.9 mL) cooled to zero degrees C was added pyridine (97 μL, 1.20 mmol) dropwise over ten minutes with stirring. Stirring was continued for one hour, allowing the temperature to rise to 10° C. Then 2.0 mL of this solution of 2-(phenylsulfonyl)ethoxycarbonyl chloride [see also, Balgobin et al., *Tetrahedron Lett.*, 22:3667 (1981)] were added dropwise over two hours to a solution of daunomycin hydrochloride (243 mg, 0.443 mmol) and pyridine (0.215 mL, 2.66 mmol) in dichloromethane (0.3 mL) with stirring at −20° C. Stirring was continued for a further ten minutes at room temperature, and the reaction mixture was diluted with chloroform (5 mL). The reaction mixture was extracted with 0.25 M aqueous HCl (2.5 mL). The organic layer was washed with 0.1 M aqueous HCl (50 mL), water (50 mL), and brine (25 mL). The organic layer was dried (MgSO$_4$ and evaporated in vacuo. The residue was purified by flash chromatography (silica, 25 percent acetone in chloroform) to give 242 mg (94 percent) of Compound 1: bright red gum; $R_f$=0.19 (silica, 20 percent acetone in chloroform); IR (thin film) $v_{max}$ 3498, 2973, 2936, 1713, 1617, 1580, 1524, 1443, 1412, 1289, 1232, 1209, 1145, 1078, 1033, 986, 732 cm$^{-1}$; $^1$H NMR (500 MHz, CDCl$_3$) δ13.97 (s, 1 H, ArOH), 13.24 (s, 1H, ArOH), 8.02 (d, J=7.7 Hz, 1H, anthraquinone), 7.89 (d, J=7.5 Hz, 2 H, phenyl), 7.77 (t, J=8.2 Hz, 1 H, anthraquinone), 7.65 (d, J=7.5 Hz, 1 H, phenyl), 7.56 (t, J=7.5 Hz, 2 H, phenyl), 7.38 (d, J=8.2 Hz, 1 H, anthraquinone), 5.47 (d, J=3.6 Hz, 1 H, OCHO-anomeric), 5.24 (br s, 1 H, NH), 4.92 (d, J=8.6 Hz, 1 H, ArCHO-sugar), 4.43 (s, 1 H, (C=O)COH), 4.33 (m, 2 H, SO$_2$CH$_2$CH$_2$OCO), 4.18 (br q, J=6.4 Hz, 1 H, CH$_3$CHO), 4.07 (s, 3 H, ArOMe), 3.76 (m, 1 H, CHOH), 3.60 (br d, J=5.4 Hz, 1 H, CHOH), 3.41 (t, J =5.9 Hz, 2 H, SO$_2$CH$_2$CH$_2$OCO), 3.20 (br d, J=18.8 Hz, 1 H, ArCH$_2$COH (C=O)), 2.88 (d, J=7.0 Hz, 1 H, ArCH$_2$COH(C=O)), 2.41 (s, 3 H, CH$_3$CHO), 2.30 (br d, J=14.9 Hz, 1 H, CHNH), 2.16 (d, J=7.5 Hz, 1 H Ar(CHOR)CH$_2$), 2.11 (dd, J=14.9, 4.0 Hz, 1 H, CH$_2$CHNH), 1.79–1.67 (m, 2 H, CH$_2$); $^{13}$C NMR (125 MHz, CDCl$_3$) δ 212.0, 187.0, 186.6, 161.0, 156.3, 155.8, 154.5, 139.4, 135.7, 135.4, 134.4, 133.9, 129.3, 121.8, 128.0, 120.8, 119.8, 118.4, 111.4, 111.2, 100.5, 70.0, 69.2, 67.0, 58.0, 56.6, 55.4, 47.0, 34.9, 33.4, 30.9, 29.7, 24.9, 16.7; HRMS (FAB$^+$) for C$_{36}$H$_{37}$NO$_{14}$SCs (M+Cs), calcd 872.0989, found 872.0963.

Screening Against Cell Lines

Compound 1 was screened against a panel of cancerous cell lines as target cells and "normal", non-cancerous cell preparations. This screening utilized a sulforhodamine B cytotoxicity assay as discussed below, with the results being presented in Table 1, hereinbefore.

SULFORHODAMINE B CYTOTOXICITY ASSAY

1. Preparation of target cells in 96-well plates
   a. Drain media from TTs flask of target cell line(s) and carefully wash cell monolayer two times with sterile PBS (approximately 5 mL per wash)
   b. Add 5 mL trypsin/EDTA solution and wash monolayer for approximately 15 seconds
   c. Drain all but approximately 1 mL of trypsin/EDTA from flask, cap flask tightly, and incubate at 37° C. for approximately two to five minutes until cells come loose.
   d. Add 10–15 mL tissue culture (T.C.) medium (RPMI 1640 plus 10 percent fetal calf serum and 2 mM L-glutathione) to flask and pipet gently up and down to wash cells.
   e. Remove a ½ mL aliquot of the cell suspension and transfer to a glass 12×75 mm culture tube for counting.
   f. Count cells on a hemacytometer using trypan blue, and determine percent viability.
   g. Adjust volume of cell suspension with T.C. media to give a density of 1×10$^5$ cells/mL.
   h. Add 100 µL of T.C. medium to wells A1 and B1 of a 96-well plate for blanks.
   i. Add 100 µL of cell suspension to the remaining wells of the 96-well plates.
   j. Incubate plates for 24 hours at 37° C., 5–10 percent CO$_2$ in a humidified incubator.
2. Preparation of sample drugs and toxic control
   a. Stock drug solutions were prepared by dissolving drug in the appropriate solvent (determined during chemical characterization studies) and sterile filtering the drug-solvent solution through a sterile 0.2 µ filter unit. An aliquot was taken from each filtered drug solution and the O.D. was measured to determine the drug concentration.
   b. Dilute the stock drug solution prepared above with T.C. medium to the desired initial concentration (10$^{-2}$–10$^{-4}$M). A minimum volume of 220 µL of diluted drug is required per 96-well plate used in the assay.
   c. Prepare toxic control by diluting stock doxorubicin solution to 10$^{-7}$ to 10$^{-9}$M in T.C. medium. A minimum volume of 300 µL is required per 96-well plate.
3. Addition of Sample Compounds and Controls to 96-well Plates
   a. Remove and discard 100 µL of T.C. medium from the wells in Column #2 of the 96-well plate using a multi-channel pipettor and sterile tips.
   b. Add 100 µL of the initial compound dilution to adjacent duplicate wells in Columns #2. (Four materials can be tested in duplicate per 96-well plate.)
   c. Remove 10 µL of diluted compound from the wells in Column #2 and transfer to the corresponding wells in Column #3. Mix by pipetting up and down gently approximately five times.
   d. Transfer 10 µL to the appropriate wells in Column #4 and continue to make 1:10 dilutions of compound across the plate through Column #12.
   e. Remove and discard 100 µL of medium from wells F1, G1, and H1. Add 100 µL of toxic control (Doxorubicin diluted in T.C. medium) to each of these wells.
   f. Incubate (37° C., 5–10 percent CO$_2$ in humidified incubator) plates for a total of 72 hours. Check plates at 24 hour intervals microscopically for signs of cytotoxicity.
4. Cell Fixation
   a. Adherent cell lines:
      1. Fix cells by gently layering 25 µL of cold (4° C.) 50 percent trichloroacetic acid (TCA) on top of the growth medium in each well to produce a final TCA concentration of 10 percent.
      2. Incubate plates at 4° C. for one hour.
   b. Suspension cell lines:
      1. Allow cells to settle out of solution.
      2. Fix cells by gently layering 25 µL of cold (4° C.) 80 percent TCA on top of the growth medium in each well.
      3. Allow cultures to sit undisturbed for five minutes.
      4. Place cultures in 4° C. refrigerator for one hour.
   c. Wash all plates five times with tap water.
   d. Air dry plates.
5. Staining Cells
   a. Add 100 µL of 0.4 percent (wt./vol.) Sulforhodamine B (SRB) dissolved in 1 percent acetic acid to each well of 96-well plates using multichannel pipertot.
   b. Incubate plates at room temperature for 30 minutes.
   c. After the 30 minute incubation, shake plates to remove SRB solution.
   d. Wash plates two times with tap water and 1× with 1 percent acetic acid, shaking out the solution after each wash. Blot plates on clean dry absorbent towels after last wash.
   e. Air dry plates until no standing moisture is visible.
   f. Add 100 µL of 10mM unbuffered Tris base (ph 10.5) to each well of 96-well plates and incubate for five minutes on an orbital shaker.

g. Read plates on a microtiter plate reader at 540 nM.

IC$_{50}$ values; i.e., the concentration of Compound required to kill one-half of the treated cells, were then calculated.

The cell lines assayed are listed below along with their respective sources:

| Cell Line | Source and Type |
|---|---|
| UCLA P-3 | Dr. R. Reisfeld of The Scripps Research Institute, and originally obtained from Dr. D. Morton, University of California, Los Angeles. P-3 is a human non-small cell lung carcinoma cell line. |
| PBL | Human peripheral blood lymphocytes (R.W. Johnson Pharmaceutical Research Institute, La Jolla, CA) |
| HMEC | Human mammary epithelial cells |
| NHDF | Normal human dermal fibroblasts |
| NHEM | Normal human epidermal melanocytes (Clonetics Corporation, San Diego, CA) |

All other cells or cell lines were obtained from the American Type Culture Collection (ATCC) (all except CHO cells are human or mouse cancer cell lines as described by the ATCC).

The results of this study are shown in Table 1, hereinbefore.

In Vivo Mouse Study

The data of FIG. 1 illustrate an in vivo study using Compound 1. Here, groups of 6-10 week old, female Balb/c BYJ mice (obtained from The Scripps Research Institute breeding colony, La Jolla, Calif.) (8 per group) were inoculated with 5×10$^5$ cells of the EMT6 tumor cell line, a mammary tumor. The mice were then treated with normal saline (control) or normal saline containing 15 mg/kg of Compound 1 (study) on days 1, 5 and 9 after the inoculation.

The average tumor volume was then calculated for each group of mice. As can be seen from the graph of FIG. 1, by day 8 post inoculation, there was a slight difference in the average volume of the tumors, with the study group having a lower tumor burden. Between days 14 and 16, the treated mice had about one-third the tumor burden of the control group. By day 20 post inoculation, the control group's average tumor volume was about twice that of the study group.

The foregoing is intended as illustrative of the present invention but not limiting. Numerous variations and modifications may be effected without departing from the true spirit and scope of the novel concepts of the invention.

We claim:

1. A chemotherapeutic process for killing or inhibiting the growth of cancerous cells that comprises contacting cancerous cells to be killed or whose growth is to be inhibited in vitro in an aqueous medium suitable for growth of those cells with a chemotherapeutic amount of an active agent, said active agent having a structure that corresponds to structural Formula I wherein Ar is phenyl, 1-naphthyl or 2-naphthyl,

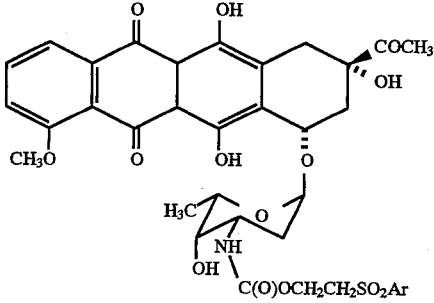

and maintaining said contact in said aqueous medium for a time period sufficient for the contacted cells to be killed or their growth inhibited.

2. A chemotherapeutic process for killing or inhibiting the growth of cancerous cells that comprises contacting cancerous cells to be killed or whose growth is to be inhibited in vivo in a host mammal with a chemotherapeutic amount of an active agent by administration of a pharmaceutical composition containing said active agent dissolved or dispersed in a physiologically tolerable diluent to said mammal, said active agent having a structure that corresponds to structural Formula I wherein Ar is phenyl, 1-naphthyl or 2-naphthyl,

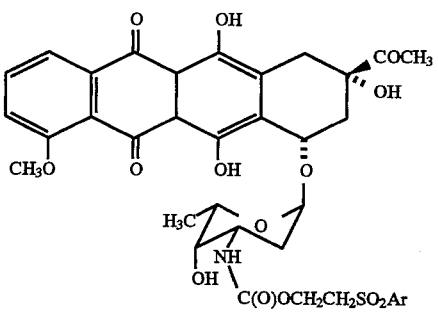

and maintaining said contact for a time period sufficient for the contacted cells to be killed or their growth inhibited.

3. The process according to claim 2 wherein said active agent has a structure that corresponds to the formula

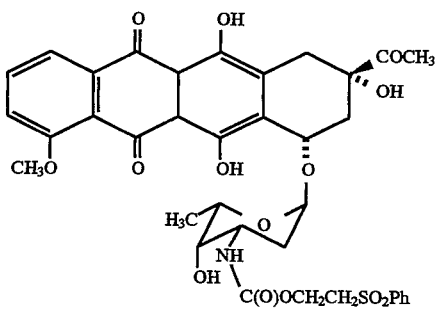

wherein Ph is phenyl.

4. The process according to claim 2 wherein said administration is repeated.

* * * * *